United States Patent [19]

Meul et al.

[11] Patent Number: 5,093,503

[45] Date of Patent: * Mar. 3, 1992

[54] PROCESS FOR THE PRODUCTION OF THIOTETRONIC ACID

[75] Inventors: Thomas Meul; Leander Tenud, both of Visp, Switzerland

[73] Assignee: Lonza Ltd., Gampel/Valais, Switzerland

[*] Notice: The portion of the term of this patent subsequent to Mar. 5, 2008 has been disclaimed.

[21] Appl. No.: 580,586

[22] Filed: Sep. 11, 1990

Related U.S. Application Data

[63] Continuation of Ser. No. 76,855, Jul. 23, 1987, Pat. No. 4,997,957, which is a continuation of Ser. No. 818,766, Jan. 14, 1986, abandoned.

[30] Foreign Application Priority Data

Jan. 16, 1985 [CH] Switzerland ............................ 193/85

[51] Int. Cl.$^5$ .......................................... C07D 333/36
[52] U.S. Cl. ................................................ 549/62
[58] Field of Search .......................................... 549/62

[56] References Cited

U.S. PATENT DOCUMENTS

| | | |
|---|---|---|
| 2,453,103 | 11/1948 | Turnbull . |
| 2,535,010 | 12/1950 | Croxall et al. . |
| 2,784,191 | 3/1957 | Fischer et al. . |
| 3,701,803 | 10/1972 | Boosen . |
| 4,118,396 | 10/1978 | Pifferi et al. . |
| 4,124,594 | 11/1978 | Monguzzi et al. . |
| 4,173,569 | 11/1979 | Banfi et al. . |
| 4,997,957 | 3/1991 | Meul et al. ............ 549/62 |

FOREIGN PATENT DOCUMENTS

| | | |
|---|---|---|
| 0028709 | 10/1980 | European Pat. Off. . |
| 0060808 | 9/1982 | European Pat. Off. . |
| 0192255 | 8/1986 | European Pat. Off. . |
| 850007 | 12/1951 | Fed. Rep. of Germany . |
| 2214540 | 10/1972 | Fed. Rep. of Germany . |
| 539611 | 9/1973 | Switzerland . |
| 539631 | 9/1973 | Switzerland . |
| 557644 | 1/1975 | Switzerland . |
| 840658 | 7/1960 | United Kingdom . |
| 1266092 | 3/1972 | United Kingdom . |
| 1266093 | 3/1972 | United Kingdom . |
| 1299298 | 12/1972 | United Kingdom . |
| 1299299 | 12/1972 | United Kingdom . |
| 1362143 | 7/1974 | United Kingdom . |
| 1362144 | 7/1974 | United Kingdom . |

OTHER PUBLICATIONS

Benary, Erich "Uber Thio-tetronsaure und Derivate", *Chemische Berichte*, Band 46, (1913), pp. 2103–2107.
Hopff et al. "N-Aryl-α-Pyrrolidinones", Ger. 850,007, Sep. 22, 1952, CA vol. 52, 11124g.
MacKenzie et al. "Preparation of Ketals. A Reaction Medium", *J.O.C.S.*, vol. 20, No. 12 (Jul. 20, 1955), pp. 1695–1696.
Cram et al. "Mold Metabolites. IX. Contribution to the Elucidation of the Structure of Althiomycin", *Journal of the American Chemical Society*, vol. 85, (May 20, 1963), pp. 1430–1437.
Sidgwick, N. V. *The Organic Chemistry of Nitrogen*, 3rd ed. (Oxford, England, Clarendon Press, 1966) p. 637.
Mortensen et al. "Preparation and Tautomeric Structures of Some Potential Dihydroxylthiophenes", *Tetrahedron*, vol. 27 (1971), pp. 3839–3851.
King et al. "4-Hydroxy-2,5-dimethyl-2,3-dihydrothiophen-3-one, useful as a flavoring", Ger. Offen. 2,214,540, CA vol. 73, 1973, 29615a.
Lowe et al. "Synthesis of a β-Lactam Related to the Cephalosporins", *Journal of Chemical Society*, Perkin Trans. I, (1973), pp. 2907–2910.
Macierewicz, B. "Enolization of 2.4–Dioxotetrahydrothiophene", *Roczniki Chemii*, vol. 47, No. 10, (1973), pp. 1735–1741.
Ho et al. "Cleavage of Esters and Ethers with Iodotrimethylsilane", *Angew. Chem.* Int. Ed. Engl., vol. 15, No. 12, (1976), pp. 774–775.
Pifferi et al. "Cyclic Gaba-Gabob Analogues", *Il Farmaco-Ed. Sc.*, vol. 32, fasc. 8 (1977), pp. 602–613.
Wang et al. "Total Synthesis of (±)-Thiolactomycin", *Tetrahedron*, vol. 25, No. 46 (1984), pp. 5243–5246.
Kohler, H., Dissertation at the University of Bayreuth in 1985, Munchberg, Germany.
Daioni, R. "3,4'-Bi-2H-pyrrole-2,2'-dione hydro derivates", Eur. Pat. Appl. 192,255, (1986) CA vol. 105, 1986, 226341k.

*Primary Examiner*—Alan Siegel
*Attorney, Agent, or Firm*—Fisher, Christen & Sabol

[57] ABSTRACT

Process for the production of thiotetronic acid wherein 4-chloroacetoacetic acid chloride is reacted with hydrogen sulfide in the presence of an amine.

22 Claims, No Drawings

PROCESS FOR THE PRODUCTION OF THIOTETRONIC ACID

This application is a continuation of Ser. No. 076,855, filed Jul. 23, 1987, now U.S. Pat. No. 4,997,957 which is a continuation of Ser. No. 818,766, filed Jan. 14, 1986, now abandoned.

BACKGROUND OF THE INVENTION

1. Field Of The Invention

The invention relates to a process for the production of thiotetronic acid. 2. Prior Art It has been reported that thiotetronic acid has been used as an intermediate product for the production of (+) thiolactomycin, an antibiotic having a broad effective spectrum *Tetrahedron Letters*, Vol. 25, No. 46, pp. 5243 to 5246, (1984) discloses that the dimethyl homologue compound of thiotetronic acid can be used to make (±)-thiolactomycin, an antibiotic having a broad effective spectrum, and the diethyl homologue compound of thiotetronic acid can be used to make thiotetromycin. Accordingly, the *Tetrahedron Letters* letter would cause one skilled in the art to recognize the possible use of thiotetronic acid for the production of a thiolactomycin derivative.

From E. Benary, Chemische Berichte 46, 2103 (1913), it is known to produce thiotetronic acid starting out from acetylthioglycoyl chloride as a result of reaction thereof with sodium malonic ester and subsequently ring closure and water treatment D. B. Macierewicz, Rocz. Chem. 47, 1735, (1973), reproduced the reaction of E. Benary and obtained at the same time thiotetronic acid at a yield of 30.3 percent, related to the acetylthioglycoyl chloride used. Another possibility for synthesis is set out in J. Z. Mortensen et al., Tetrahedron, 27, 3839, (1971). Starting out from 2,4-dibromothiophene, the thiotetronic acid is obtained in a yield of 46.2 percent by way of three steps as a result of reaction with butyl lithium and t-butylperbenzoate.

In the case of all of the above-identified traditional syntheses, the yields thereof are much too low for a technical or commercial process. Moreover, the processes are hindered by cumbersomeness, expensive educts and by reagents that are difficult to handle.

BROAD DESCRIPTION OF THE INVENTION

An object of the invention is to provide a process for the production of thiotetronic acid which is distinguished by high yields, favorable educts and simple procedure steps. Other objects and advantages of the invention are set out herein or are obvious herefrom to one skilled in the art.

The objects and advantages of the invention are achieved by the process of the invention.

The invention involves preparing thiotetronic acid by treating 4-chloroacetoacetic acid chloride with hydrogen sulfide in the presence of an amine as a base.

DETAILED DESCRIPTION OF THE INVENTION

Effectively one starts with diketene which is converted in a known manner (e.g., published European Patent Application No. 28 709) by chlorination into 4-chloroacetoacetic acid chloride, which can then be adduced in situ for further conversion.

Effectively, operation is conducted in a solvent or solvents. The halogenated hydrocarbons, such as, methylene chloride or chloroform, are advantageous. Methylene chloride is particularly suitable.

As an organic amine, effectively primary, secondary and tertiary amines as well as ammonia and guanidine are used. Preferably, tertiary amines are used; in an especially preferred manner, triethylamine is used.

Hydrogen sulfide is advantageously used in gaseous form.

The educt ratio, in moles, of 4-chloroacetoacetic acid chloride to hydrogen sulfide to amine, is effectively between 1:2:2 and 1:4:3, and preferably between 1:2.5:2 and 1:3.5:2.2.

In order to avoid reaction of the 4-chloroacetoacetic acid chloride with the amines to 4-chloroacetoacetic acid amides or a base catalyzed dimerization into dichlorodehydroacetic acid, the process effectively is conducted in such a way that the acid chloride solution first of all is reacted with hydrogen sulfide and subsequently with the amine. Just as important is the ratio (in moles) of $H_2S$ to amine, for only in the case of an equimolar ratio, better still in the case of excess $H_2S$, will the formation of the above mentioned undesirable by-products be suppressed. The conversion of the acid chloride in the thiotetronic acid is completed immediately after the addition of the amine.

The conversion of the 4-chloroacetoacetic acid chloride is carried out effectively at a temperature of 0° to −40° C., preferably at −10° to −20° C.

The reprocessing of the reaction mixture can be conducted by separation of the solvent as a result of concentration or distillation and by subsequent extraction of the target product from the residue with a suitable solvent or solvents. Suitable solvents are ethereal solvents, such as, tetrahydrofuran (THF), dioxane or diethyl ether. Diethyl ether is particularly advantageously.

Effectively, the extract solution is treated prior to evaporation for the separation of small quantities of dimeric anhydrothiotetronic acid with an absorption agent, such as, silica gel. After evaporation and drying, the thiotetronic acid can be obtained as a crystalline product.

As used herein, all parts, percentages, ratios and proportions are on a weight basis unless otherwise stated herein or otherwise obvious herefrom to one skilled in the art.

EXAMPLE

From 8.5 g (0.1 mole) of diketene and 7.1 g (0.1 mole) of chlorine, dissolved in 100 ml of methylene chloride, 4-chloroacetoacetic acid chloride was produced according to a known process (i.e., published European Patent Application No. 28,709). This solution was diluted with 500 ml of methylene chloride and was saturated at −15° C. with a gaseous hydrogen sulfide. To this solution, a solution of 20.2 g (0.2 mole) of triethylamine in 180 ml of methylene chloride was added drop by drop at −10° C. within 1.5 hours. (The educt ratio of 4-chloroacetoacetic acid chloride: $H_2S$:triethylamine was 1:3:2.) The temperature of the reaction solution was allowed to rise to room temperature, the solvent was distilled off using a rotation evaporator and the thiotetronic acid was dissolved out of the firm residue in a Soxhlet-extractor with 200 ml of ether. This ether solution was filtered by means of a column filled with silica gel. 7.0 g of orange colored, crystalline product with a content (HPLC) of 88.0 percent was obtained. This corresponded to 6.2 g of 100 percent product (=53.4 percent yield). Melting point: 115° C.

$^1$H-NMR spectrum (300 MHz, DMSO-d$_6$) δ=4.04 (d,2H,J=1,0Hz), 5.36 (t,1H), 12.55 (used s,1H)

By way of summary, the invention involves a process for the production of thiotetronic acid by the reaction of 4-chloroacetoacetic acid chloride with hydrogen sulfide in the presence of an amine.

What is claimed is:

1. Process for the production of thiotetronic acid comprising reacting 4-chloroacetoacetic acid chloride with hydrogen sulfide in the presence of an amine.

2. Process as claimed in claim 1 wherein the amine is a primary amine, a secondary amine, a tertiary amine, ammonia or guanidine.

3. Process as claimed in claim 2 wherein the amine is a tertiary amine.

4. Process as claimed in claim 3 wherein the reaction is operated in a solvent.

5. Process as claimed in claim 4 wherein the solvent is a halogenated hydrocarbon.

6. Process as claimed in claim 5 wherein the educt ratio, in moles, of 4-chloroacetoacetic acid chloride to hydrogen sulfide to amine is between 1:2:2 and 1:4:3.

7. Process as claimed in claim 6 wherein the reaction is carried out at a temperature between 0° and −40° C.

8. Process as claimed in claim 1 wherein the amine is a tertiary amine.

9. Process as claimed in claim 1 wherein the reaction is operated in a solvent.

10. Process as claimed in claim 9 wherein the solvent is a halogenated hydrocarbon.

11. Process as claimed in claim 1 wherein the educt ratio, in moles, of 4-chloroacetoacetic acid chloride to hydrogen sulfide to amine is between 1:2:2 and 1:4:3.

12. Process as claimed in claim 1 wherein the reaction is carried out at a temperature between 0° and −40° C.

13. Process as claimed in claim 10 wherein the solvent is methylene chloride or chloroform.

14. Process as claimed in claim 8 wherein the tertiary amine is triethylamine.

15. Process as claimed in claim 9 wherein the hydrogen sulfide is used in gaseous form to saturate the solution of 4-chloroacetoacetic acid chloride in a solvent and wherein then a solution of the amine in a solvent is added to the solution of 4-chloroacetoacetic acid chloride and hydrogen sulfide.

16. Process as claimed in claim 1 wherein the hydrogen sulfide and the 4-chloroacetoacetic acid chloride are contacted and then the amine is contacted with the hydrogen sulfide and the 4-chloroacetoacetic acid chloride.

17. Process as claimed in claim 1 wherein the educt ratio, in moles of 4-chloroacetoacetic acid chloride to hydrogen sulfide to amine is between 1:2.5:2 and 1:3.5:2.2.

18. Process as claimed in claim 1 wherein the reaction is carried out at a temperature between −10° and −20° C.

19. Process as claimed in claim 9 wherein the solvent is removed from the reaction mixture by concentration on distillation, the thiotetronic acid is separated by extraction by means of an ethereal solvent, and the extraction solution is evaporated to provide the thiotetronic acid.

20. Process as claimed in claim 19 wherein the ethereal solvent is tetrahydrofuran, dioxane or diethyl ether.

21. Process as claimed in claim 19 wherein the extraction solution is filtered using an absorption agent before the evaporation step.

22. Process as claimed in claim 21 wherein the absorption agent is silica gel.

* * * * *